(12) United States Patent
Kluger et al.

(10) Patent No.: US 10,549,099 B2
(45) Date of Patent: Feb. 4, 2020

(54) ELECTRONIC PERIPHERAL NERVE STIMULATION

(71) Applicant: University of Utah Research Foundation, Salt Lake City, UT (US)

(72) Inventors: David Kluger, Salt Lake City, UT (US); Christopher Duncan, Salt Lake City, UT (US); David Page, Salt Lake City, UT (US); Gregory Clark, Salt Lake City, UT (US); Tyler Davis, Salt Lake City, UT (US); Suzanne Wendelken, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 213 days.

(21) Appl. No.: 15/583,568

(22) Filed: May 1, 2017

(65) Prior Publication Data

US 2017/0312522 A1    Nov. 2, 2017

Related U.S. Application Data

(60) Provisional application No. 62/329,998, filed on Apr. 29, 2016.

(51) Int. Cl.
*A61N 1/36* (2006.01)
*A61N 1/06* (2006.01)
*A61N 1/372* (2006.01)

(52) U.S. Cl.
CPC .......... *A61N 1/36071* (2013.01); *A61N 1/06* (2013.01); *A61N 1/36157* (2013.01); *A61N 1/36171* (2013.01); *A61N 1/37247* (2013.01)

(58) Field of Classification Search
CPC .. A61N 1/06; A61N 1/36071; A61N 1/36157; A61N 1/36171; A61N 1/37247
See application file for complete search history.

(56) References Cited

U.S. PATENT DOCUMENTS

| | | |
|---|---|---|
| 5,215,088 A | 6/1993 | Normann et al. |
| 8,359,083 B2 | 1/2013 | Clark et al. |
| 8,588,884 B2 | 11/2013 | Hegde et al. |
| 8,630,711 B1 * | 1/2014 | Wark ................... A61N 1/0551 600/29 |

(Continued)

OTHER PUBLICATIONS

Ackermann Jr. et al.; "Conduction Block of Peripheral Nerve Using High Frequency Alternating Currents Delivered Through an Intrafascicular Electrode." Muscle Nerve; NIH Public Access; Jan. 2010; vol. 41, Issue 1; pp. 117-119.

(Continued)

*Primary Examiner* — George Manuel
(74) *Attorney, Agent, or Firm* — Thorpe North & Western, LLP

(57) ABSTRACT

A technology is described for an electronic peripheral nerve stimulation system. The electronic nerve stimulation system can include a stimulation device and an electrode array. The stimulation device can be operable to generate a high-frequency alternating current. The electrode array can be operable to apply the high-frequency alternating current received from the stimulation device to selected subpopulations of peripheral nerve fibers within a peripheral nerve to block transmission of neural signals along the selected subpopulations of peripheral nerve fibers within the peripheral nerve.

25 Claims, 5 Drawing Sheets

(56) References Cited

U.S. PATENT DOCUMENTS

| | | |
|---|---|---|
| 8,865,288 B2 | 10/2014 | Bhandari et al. |
| 8,886,279 B2 | 11/2014 | Tathireddy et al. |
| 8,983,614 B2 | 3/2015 | Kilgore et al. |
| 9,149,635 B2 | 10/2015 | Denison et al. |
| 9,220,895 B2 | 12/2015 | Siff et al. |
| 9,295,841 B2 | 3/2016 | Fang et al. |
| 9,345,538 B2 | 3/2016 | Deem et al. |
| 9,364,661 B2 | 6/2016 | Kilgore et al. |
| 9,387,322 B2 | 7/2016 | Bhadra et al. |
| 2009/0204173 A1* | 8/2009 | Fang ............... A61N 1/36071 607/46 |
| 2010/0268055 A1 | 10/2010 | Jung et al. |
| 2013/0090542 A1 | 4/2013 | Kipke et al. |
| 2013/0110194 A1* | 5/2013 | Wei ................. A61N 1/36071 607/46 |
| 2014/0074176 A1 | 3/2014 | Jansen et al. |
| 2014/0128950 A1 | 5/2014 | Thota et al. |
| 2014/0324129 A1* | 10/2014 | Franke .............. A61N 1/3606 607/62 |
| 2015/0141786 A1 | 5/2015 | Durand et al. |
| 2017/0007813 A1 | 1/2017 | Negi et al. |

OTHER PUBLICATIONS

Kilgore et al.; "Reversible Nerve Conduction Block Using Kilohertz Frequency Alternating Current." Neuromodulation; NIH Public Access; Apr. 2014; vol. 17, Issue 3; pp. 242-255.

Zhu et al.; "Research on Peripheral Nerve Conduction Block by High Frequency Alternating Current Stimulation." $5^{th}$ International Conference on Biomedical Engineering and Infomatics; IEEE; Oct. 16-18, 2012; pp. 582-586.

\* cited by examiner

ELECTRONIC PERIPHERAL NERVE STIMULATION

RELATED APPLICATION(S)

This application claims the benefit of U.S. Provisional Application No. 62/329,998, filed Apr. 29, 2016, which is incorporated herein by reference.

GOVERNMENT INTEREST

None.

BACKGROUND

For purposes of this application, electrical stimulation of neurons is a procedure that uses an electrical current to stimulate neuronal tissues in order treat pain. Peripheral nerve stimulation (PNS) and spinal cord stimulation (SCS) are two types of electrical stimulation of neurons. In both cases, a small pulse generator sends electrical pulses to the nerves (in PNS) or to the spinal cord (in SCS). The electrical pulses can interfere with neuronal electrical impulses, thereby reducing a sensation of pain in a human subject. One or more electrodes can be inserted under the patient's skin (i.e., percutaneously). The electrodes can be attached to the subject's nerves or spinal canal. The electrodes can be connected to a stimulator, which produce the electrical pulses. The delivery of electrical pulses from the stimulator to the electrodes can reduce the subject's pain in areas directly or indirectly innervated by neurons stimulated by the electrodes. Despite some advances with such technologies, current options tend to have limited effectiveness or can result in undesirable loss of sensation, loss of motor control, or other side-effects.

SUMMARY

A technology is described for delivering high-frequency alternating current to tissues and peripheral nerves via electrodes to achieve pain blocking. In one example, there is provided an electronic peripheral nerve stimulation system comprising a stimulation device and an electrode array. The stimulation device can be operable to generate a high-frequency alternating current. The electrode array operable to apply the high-frequency alternating current received from the stimulation device to selected subpopulations of peripheral nerve fibers within a peripheral nerve to block transmission of neural signals along the selected subpopulations of peripheral nerve fibers within the peripheral nerve.

In one example of the electronic peripheral nerve stimulation system, the electronic nerve stimulation system further comprises a power supply that provides direct current or alternating current to the stimulation device for generation of the high-frequency alternating current In one example, there is provided a method for electronically stimulating selected subpopulations of peripheral nerve fibers within a peripheral nerve, the method including receiving a current from a power source. The method can further include generating a high-frequency alternating current using the current received from the power source. The method can also include providing the high-frequency alternating current to an implantable electrode array. The implantable electrode array can be operable to apply the high-frequency alternating current to stimulate selected subpopulations of peripheral nerve fibers within a peripheral nerve of a subject for blocking transmission of neural signals along the selected subpopulations of peripheral nerve fibers within the peripheral nerve.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

Figure 1:
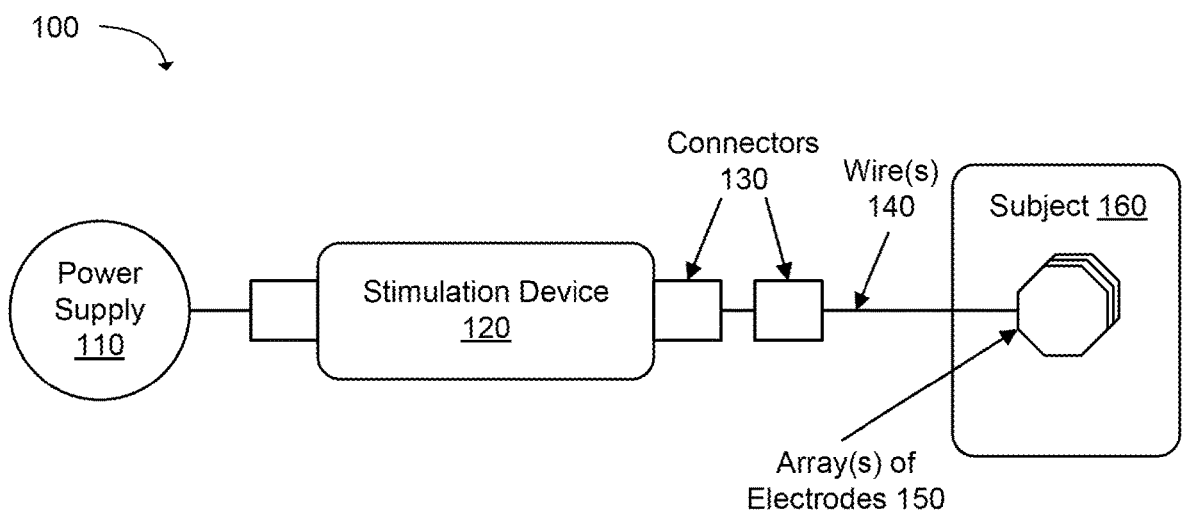
FIG. 1 illustrates an electronic peripheral nerve stimulation system in accordance with an example.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

In describing and claiming the present invention, the following terminology will be used.

The singular forms "a," "an," and "the" include plural referents unless the context clearly dictates otherwise. Thus, for example, reference to "an electrode" includes reference to one or more of such features and reference to "subjecting" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of" For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

An initial overview of technology embodiments is provided below and specific technology embodiments are then described in further detail. This initial summary is intended to aid readers in understanding the technology more quickly, but is not intended to identify key or essential features of the technology, nor is it intended to limit the scope of the claimed subject matter.

The present technology relates to an electronic peripheral nerve stimulation system that can perform high-frequency alternating current peripheral nerve stimulation with an array of chronically-implanted intrafascicular peripheral nerve electrodes. These electrodes can selectively block transmission of neural signals along peripheral nerve fibers within a peripheral nerve of a human subject. The peripheral nerve is an enclosed, cable-like bundle of peripheral nerve fibers (or axons) in a peripheral nervous system of the subject. The peripheral nerve can include non-nerve connective tissue as well as peripheral nerve fibers related to muscle control, sensation and pain. The application of the high-frequency alternating current to selected peripheral nerve fibers within the peripheral nerve via the array of intrafascicular peripheral nerve electrodes can function to selectively block the transmission of neural signals to and from the subject's brain. In other words, the application of the high-frequency alternating current to selected peripheral nerve fibers within the peripheral nerve via the array of intrafascicular peripheral nerve electrodes can function to selectively block subpopulations of peripheral nerve fibers within the peripheral nerve of the subject. The subpopulations of peripheral nerve fibers that are blocked within the peripheral nerve can be selected based on the needs of the subject. For example, selected subpopulations of peripheral nerve fibers within the peripheral nerve which are related to pain can be blocked by applying the high-frequency alternating current via the array of intrafascicular peripheral nerve electrodes, while other selected subpopulations of peripheral nerve fibers within the peripheral nerve related to sensation and/or motor function can be unaffected (i.e., the high-frequency alternating current is not applied to these other selected subpopulations of peripheral nerve fibers within the peripheral nerve). This can be accomplished be selectively energizing corresponding subpopulations of electrodes within the array of electrodes.

In previous solutions, high-frequency alternating current techniques involved targeting an entire peripheral nerve in a subject. These previous high-frequency alternating current techniques caused non-specific nerve blockades across most or the entire peripheral nerve. In other words, the previous solutions involved shutting down the entire peripheral nerve in order to block pain for the subject. Although this can often reduce or eliminate pain, significant side-effects such as loss of motor control and sensation can also result. In contrast, the electronic peripheral nerve stimulation system described herein can block selected subpopulations of peripheral nerve fibers in the peripheral nerve. In the electronic peripheral nerve stimulation system described herein, specific peripheral nerve fibers in the peripheral nerve can be blocked (e.g., peripheral nerves that cause pain), while other peripheral nerve fibers in the peripheral nerve (e.g., peripheral nerves that cause sensation) can be unaffected.

In addition, in previous solutions, the pain can be blocked using injections of drugs with nerve blocking agents. One disadvantage of such approach is that the subject would be poked with a needle for every treatment session. In contrast, the electronic peripheral nerve stimulation system described herein can use chronically-implanted intrafascicular peripheral nerve electrodes, which can eliminate the need for repeated drug injections for the subject.

In one example, the electronic peripheral nerve stimulation system described herein can be more effective for subjects with spasticity (in which certain muscles are continuously contracted) as compared to other conventional whole-nerve techniques. Since the electronic peripheral nerve stimulation system can potentially block only signals causing muscle fibers to undergo tetanus while leaving other muscle and sensory fibers unaffected, proper motor function can be regained while normal somato-sensation remains intact. In another example, when action potentials generated in a neuroma in an amputee subject cause pain, the electronic peripheral nerve stimulation system described herein can provide an ability to block associated peripheral nerve fibers (i.e., peripheral nerve fibers related to pain) while leaving other sensor fibers intact. In other words, the pain for the subject can be blocked while sensation for the subject remains unaffected, although in some cases sensation may be slightly reduced yet still functional.

In one example, certain pain treatments necessitate stimuli that are perceived as very intense to people with hyper sensitivities, such as allodynia or hyperalgesia. By blocking afferent neural transmissions originating from somatosensory organs whose activity can cause these hyper-sensitivities, allodynia and hyperalgesia can be treated without stimulating sensation-inducing sensory organs.

In one example, the electronic peripheral nerve stimulation system described herein can be utilized when certain subpopulations of peripheral nerve fibers within the peripheral nerve are to be blocked while remaining subpopulations of peripheral nerve fibers are to remain unaffected. The electronic peripheral nerve stimulation system described herein can be applicable to treat ailments including, but not limited to, cerebral palsy, stroke, limb amputation, allodynia, hyperalgesia or complex regional pain syndrome (CRPS).

In one example, the electronic peripheral nerve stimulation system described herein can be utilized to improve motor control of an intact body part, as well as for silencing motor fascicles in a peripheral nerve that are undergoing unwanted chronic firing, which can result in reduced spasticity. In other words, the electronic peripheral nerve stimulation system described herein can also be applicable to a direct and selective block of unwanted motor activity. In another example, unwanted pain may cause reluctance on the part of the subject to move a body part, so blocking the pain and recovering motor function in response to reduced pain can, in some cases, be a secondary and non-direct benefit of the electronic peripheral nerve stimulation system described herein.

In one example, effects of the peripheral nerve stimulation (e.g., pain blocking) can be almost immediate upon applying the high-frequency alternating current via the array of intrafascicular peripheral nerve electrodes. Although results can vary, stimulation effects are generally apparent in under one minute and often under 10 seconds. Further, the effects of the peripheral nerve stimulation can last for a duration that the peripheral nerve stimulation is active (i.e., when the high-frequency alternating current is flowing to the array of intrafascicular peripheral nerve electrodes). The application of the high-frequency alternating current to the subject's peripheral nerves can interfere with peripheral nerve impulses, thereby reducing a sensation of pain for the subject. After the peripheral nerve stimulation is turned off, the effects of the peripheral nerve stimulation can generally fade after a relatively short period of time (e.g. most often within an hour and frequently within 5 minutes). In other words, after the relatively short period of time, normal transmission of neural signals can be returned to previously blocked subpopulations of peripheral nerve fibers within the peripheral nerve of the subject. As such, the peripheral nerve stimulation described herein may not offer chronic relief from pain, which is in contrast to transcutaneous electrical nerve stimulation (TENS) which can offer pain relief for an extended period of time after the stimulation is turned off.

In one example, the high-frequency alternating current applied by the array of intrafascicular peripheral nerve electrodes to the selected subpopulations of peripheral nerve fibers can be a sinusoidal current waveform. The high-frequency alternating current can be a sinusoidal current waveform that ranges in frequency from 1 to 100 kilohertz (kHz) and in amperage from 0 to 150 micro amps (µA) in a single phase. The sinusoidal current waveform can have equal positive and negative currents, such that charge does not get injected into surrounding tissue of the subject. The sinusoidal current waveform can be a balanced biphasic stimulation signal, such that the sinusoidal current waveform is balanced about 0 volts. In addition, a shift correction can be applied to center the sinusoidal current waveform at 0 volts over a period of time. Most often this can be accomplished by having a balanced waveform about 0 mV±100 mV and in some cases ±50 mV.

In one example, the high-frequency alternating current can be ramped up starting from 0 mA to a defined current level (or treatment amperage) in accordance with a defined increase function (e.g., one µA per second). The high-frequency alternating current can be ramped up to the defined current level rather than instantaneously stepping from 0 µA to the defined current level. As a general guideline, the defined increase function can be linear or gradual and range from about 1 µA/sec to about 10 µA/sec, and in most cases from 1 µA/sec to 3 µA/sec. The ramping up of the high-frequency alternating current can prevent an onset response, in which an initial burst of current results in a large compound action potential in the nerve, which can be perceived as painful muscle contractions or painful sensations to the subject. The ramping up of the high-frequency alternating current can eliminate the onset response by gradually increasing the numbers of fibers whose activity gets silenced during a ramping period, which prevents the compound action potential in the nerve. The number of fibers affected by stimulation is directly correlated to the number of fibers that lie within an electric field centered on an electrode (or electrodes) which possesses the ability to block an axon. As current increases, so does the size of this electric field, which slowly increases the number of fibers which get silenced by stimulation.

In one example, the array of intrafascicular peripheral nerve electrodes can be chronically implanted in the subject's body via surgery. The array of intrafascicular peripheral nerve electrodes can include a plurality of intrafascicular nerve electrode tips. In one example, the intrafascicular nerve electrodes can be penetrating microneedle electrode arrays such as Utah Electrode Array (UEA), Utah Slant Electrode Arrays (USEA), Longitudinal Intrafascicular Electrode arrays (LIFE), Transverse Intrafascicular Multi-channel Electrode array (TIME), Michigan arrays, and the like. Arrays can include an M×N array of electrodes which extend from a substrate. The arrays can typically have from about 25 to 1000 electrodes, although this number can be varied based on available arrays and desired performance. All or a portion of the electrodes within the array can be individually electrically addressable. As a non-limiting example, the array of intrafascicular peripheral nerve electrodes can be a 10×10 matrix of intrafascicular nerve electrode tips having a USEA configuration. The intrafascicular nerve electrode tips can be individually coupled to the selected subpopulations of peripheral nerve fibers within the peripheral nerve. In other words, the high-frequency alternating current can be applied to the selected subpopulations of peripheral nerve fibers through the individual intrafascicular nerve electrode tips that are coupled (or in sufficient proximity) to the selected subpopulations of peripheral nerve fibers. In one example, the intrafascicular nerve electrode tips in the array of intrafascicular peripheral nerve electrodes can be distributed throughout the peripheral nerve. The intrafascicular nerve electrode tips can be oriented in locations within the peripheral nerve that are near the axons of interest that transmit signals which should be blocked.

In one example, various combinations of intrafascicular nerve electrode tips can be used to stimulate peripheral nerves in subjects using trial and error, and patient feedback can be used to mitigate or eliminate pain. The orientation of the intrafascicular nerve electrode tips can be carefully oriented through trial and error for effective pain blocking for the subject, while at the same time, causing minimal blocking of sensation and motor control for the subject.

In one example, individual intrafascicular peripheral nerve electrodes can evoke very selective activation of a relatively small set of peripheral nerve fibers (e.g., as low as one) with appropriate stimulation parameters. Therefore, the individual intrafascicular peripheral nerve electrodes can cause a peripheral nerve fiber related to sensation to be activated, but not a peripheral nerve fiber related to sensation related to motor control. As another example, the individual intrafascicular peripheral nerve electrodes can cause a first type of peripheral sensory nerve fiber (e.g., related to pain) to be activated, but not a second type of peripheral sensory nerve fiber (e.g., related to touch). In this example, since different peripheral sensory nerve fibers can convey different types of information, the individual intrafascicular peripheral nerve electrodes can be targeted to certain types of peripheral sensory nerve fibers. In another example, the individual intrafascicular peripheral nerve electrodes can function to block certain types of peripheral nerve fibers and/or sizes of peripheral nerve fibers. For example, smaller peripheral nerve fibers can carry signals related to pain, whereas larger peripheral nerve fibers can carry signals related to touch and motor control. Therefore, in this example, the individual intrafascicular peripheral nerve electrodes can function to block smaller peripheral nerve fibers (related to pain) and not block larger peripheral nerve fibers (related to touch and motor control).

In one example, the array of intrafascicular peripheral nerve electrodes can be chronically implanted to be coupled to peripheral nerve fibers in various areas of the subject's body including, but not limited to, the hands, arms, legs, feet, chest, penis, neck, and face. In some cases, the array of intrafascicular peripheral nerve electrodes can be oriented in close proximity to certain peripheral nerve targets in the subject's body rather than implanting within tissue, such as peripheral nerve targets that are in proximity to the subject's heart.

In one example, the array of intrafascicular peripheral nerve electrodes can be connected to a stimulation device and a power source. The stimulation device and the power source can be external to the subject, whereas the array of intrafascicular peripheral nerve electrodes can be implanted within the subject. The power source can provide power to the stimulation device, and the stimulation device can generate the high-frequency alternating current for transmission to the array of intrafascicular peripheral nerve electrodes. In one example, the stimulation device can provide the high-frequency alternating current to the array of intrafascicular peripheral nerve electrodes via transcutaneous wiring. Alternatively, the stimulation device can provide the high-frequency alternating current to the array of intrafascicular peripheral nerve electrodes via a wireless technology, which can eliminate the risk of infection caused by usage of transcutaneous wiring. In such cases, the stimulation device and the power source can be implanted under the skin and then the power source recharged wirelessly.

FIG. 1 illustrates an exemplary electronic peripheral nerve stimulation system 100. The electronic peripheral nerve stimulation system 100 can be configured to apply high-frequency alternating current to block transmission of neural signals to selected subpopulations of peripheral nerve fibers within a peripheral nerve of a subject 160, thereby reducing a sensation of pain for the subject 160. The electronic peripheral nerve stimulation system 100 can include a power supply 110, a stimulation device 120, an array of intrafascicular peripheral nerve electrodes 150, and connectors 130 and wire(s) 140 that communicatively couple the stimulation device 120 with the array of intrafascicular peripheral nerve electrodes 150.

The power supply 110 and/or the stimulation device 120 can be portable devices or non-portable devices. The power supply 110 can provide current to the stimulation device 120. The stimulation device 120 can utilize the current received from the power supply 110 to generate a high-frequency alternating current. The stimulation device 120 can provide the high-frequency alternating current to the array of intrafascicular peripheral nerve electrodes 150. The array of intrafascicular peripheral nerve electrodes 150 can provide the high-frequency alternating current received from the stimulation device 120 to the selected subpopulations of peripheral nerve fibers within the peripheral nerve, thereby blocking the transmission of neural signals along the selected subpopulations of peripheral nerve fibers within the peripheral nerve and reducing the sensation of pain for the subject 160.

In one configuration, the power supply 110 can provide up to ±300 volts (V) amplitude, which can be either direct current or alternating current and in the range of 0.01 hertz (Hz) to 50 kilohertz (kHz). The power supply 110 can be provided via batteries or via a wall-plug adaptor or both (e.g., wall-plug adaptor with batteries for backup). The power supply 110 can provide the direct current or alternating current to the stimulation device 120.

In one configuration, the stimulation device 120 can receive the direct current or alternating current from the power supply 110, and then generate the high-frequency alternating current. The high-frequency alternating current can be a sinusoidal current waveform that ranges in frequency from 1 to 100 kilohertz (kHz) and in amperage from 0 to 50 micro amps (mA). The sinusoidal current waveform can have equal positive and negative currents. The sinusoidal current waveform can be a balanced biphasic stimulation signal, such that the sinusoidal current waveform is balanced about 0 volts. In one example, the stimulation device can be formed of a power supply connector, central processing unit, digital-to-analog converting (DAC) circuitry, oscillator circuitry, current-control circuitry, fault-detection circuitry, output-voltage-monitoring circuitry, ground-isolation circuitry, and output connectors.

In one example, the stimulation device 120 can apply a shift correction through DAC circuitry to the high-frequency alternating current, such that the sinusoidal current waveform is centered at 0 volts over a period of time. In another example, the stimulation device 120 can include DAC, current-control, and oscillator circuitry which can ramp up the high-frequency alternating current starting from 0 mA to a defined current level in accordance with a defined increase function (e.g., one mA per second). The stimulation device 120 can ramp up the high-frequency alternating current to the defined current level rather than instantaneously stepping from 0 mA to the defined current level.

In one configuration, the stimulation device 120 can provide the high-frequency alternating current to the array of intrafascicular peripheral nerve electrodes 150. In one example, the stimulation device 120 can provide the high-frequency alternating current to the array of intrafascicular peripheral nerve electrodes 150 via the connectors 130 and the wires 140. The wires 140 can be wires that communicatively couple the stimulation device 120 and the array of intrafascicular peripheral nerve electrodes 150. In other words, a portion of the wires 140 can be inserted inside the subject 160, while a remaining portion of the wires 160 is outside the subject 160 and attached to the stimulation device 120 via the connectors 130. In an alternative example, the stimulation device 120 can provide the high-frequency alternating current to the array of intrafascicular peripheral nerve electrodes 150 via a wireless technology. In this example, the electronic peripheral nerve stimulation system 100 does not include the connectors 130 and the wires 140 as the high-frequency alternating current can be provided from the stimulation device 120 to the array of intrafascicular peripheral nerve electrodes 150 over an air interface using the wireless technology (infrared, radio or other wireless communication). Power can be provided via an implanted power source (rechargeable) and/or an inductive power supply. In yet another alternative, the stimulation device 120 and power supply 110 can be oriented entirely within the patient. The stimulation device can be programmed or reprogrammed wirelessly via a complimentary wireless transceiver.

In one configuration, the array of intrafascicular peripheral nerve electrodes 150 can receive the high-frequency alternating current from the stimulation device 120 via the wires 140 or using the wireless technology. The array of intrafascicular peripheral nerve electrodes 150 can be chronically and surgically implanted in the subject 160. The array of intrafascicular peripheral nerve electrodes 150 can be chronically implanted to be coupled to peripheral nerve fibers in various areas of the subject's body including, but not limited to, the hands, arms, legs, feet, chest, penis, neck, and face.

In one example, the array of intrafascicular peripheral nerve electrodes 150 can include a plurality of intrafascicular nerve electrode tips that are individually coupled to the selected subpopulations of peripheral nerve fibers within the peripheral nerve of the subject 160. In other words, certain intrafascicular nerve electrode tips can be coupled to the selected subpopulations of peripheral nerve fibers (e.g., peripheral nerve fibers that are related to pain), while other intrafascicular nerve electrode tips may not be coupled to other subpopulations of peripheral nerve fibers (e.g., peripheral nerve fibers that are related to sensation and motion control). Therefore, the intrafascicular nerve electrode tips in the array of intrafascicular peripheral nerve electrodes 150 can be distributed throughout the peripheral nerve, and the intrafascicular nerve electrode tips can be oriented in locations within the peripheral nerve that have low impedance (i.e., strong signals).

Although the intrafascicular nerve electrodes can have various geometry, in one example, the electrodes can be needle shaped electrodes to allow penetration into nerve bundles and to result in intrafascicular placement of electrode contact areas. Non-limiting examples of suitable electrodes can include Utah electrode arrays (UEA), Slant Utah electrode arrays (USEA), Michigan planar arrays, Transverse Intrafascicular Multichannel Electrodes (TIMEs), Longitudinal Intrafascicular Electrodes (LIFEs) and the like. Such arrays are known and can be formed by those skilled in the art with reference to U.S. Pat. Nos. 5,215,088; 8,359,083; 8,865,288; 8,886,279; U.S. Patent Application Publication No. US-2017-0007813-A1, US-2015-0141786-A1, US-2013-0090542-A1, and related literature. As a general guideline, such microneedle electrode arrays can have electrodes with high aspect ratio needle structures. Needle aspect ratios can range from 1:1 to 200:1, and often greater than 8:1, while heights generally range from 10 to 1500 μm. Furthermore, each array can generally have a length and width from about 2 mm to 10 mm.

In one example, the array of intrafascicular peripheral nerve electrodes 150 can apply the high-frequency alternating current to selected subpopulations of peripheral nerve fibers within the peripheral nerve to block pain for the subject 160, and the array of intrafascicular peripheral nerve electrodes 150 may not apply the high-frequency alternating current to selected subpopulations of peripheral nerve fibers within the peripheral nerve to preserve sensation and motor function for the subject 160. In one example, the transmission of neural signals along the selected subpopulations of peripheral nerve fibers can be blocked as long as the array of intrafascicular peripheral nerve electrodes 150 applies the high-frequency alternating current, and the transmission of neural signals along the selected subpopulations of peripheral nerve fibers can be unblocked when the array of intrafascicular peripheral nerve electrodes 150 stops applying the high-frequency alternating current.

Figure 2:
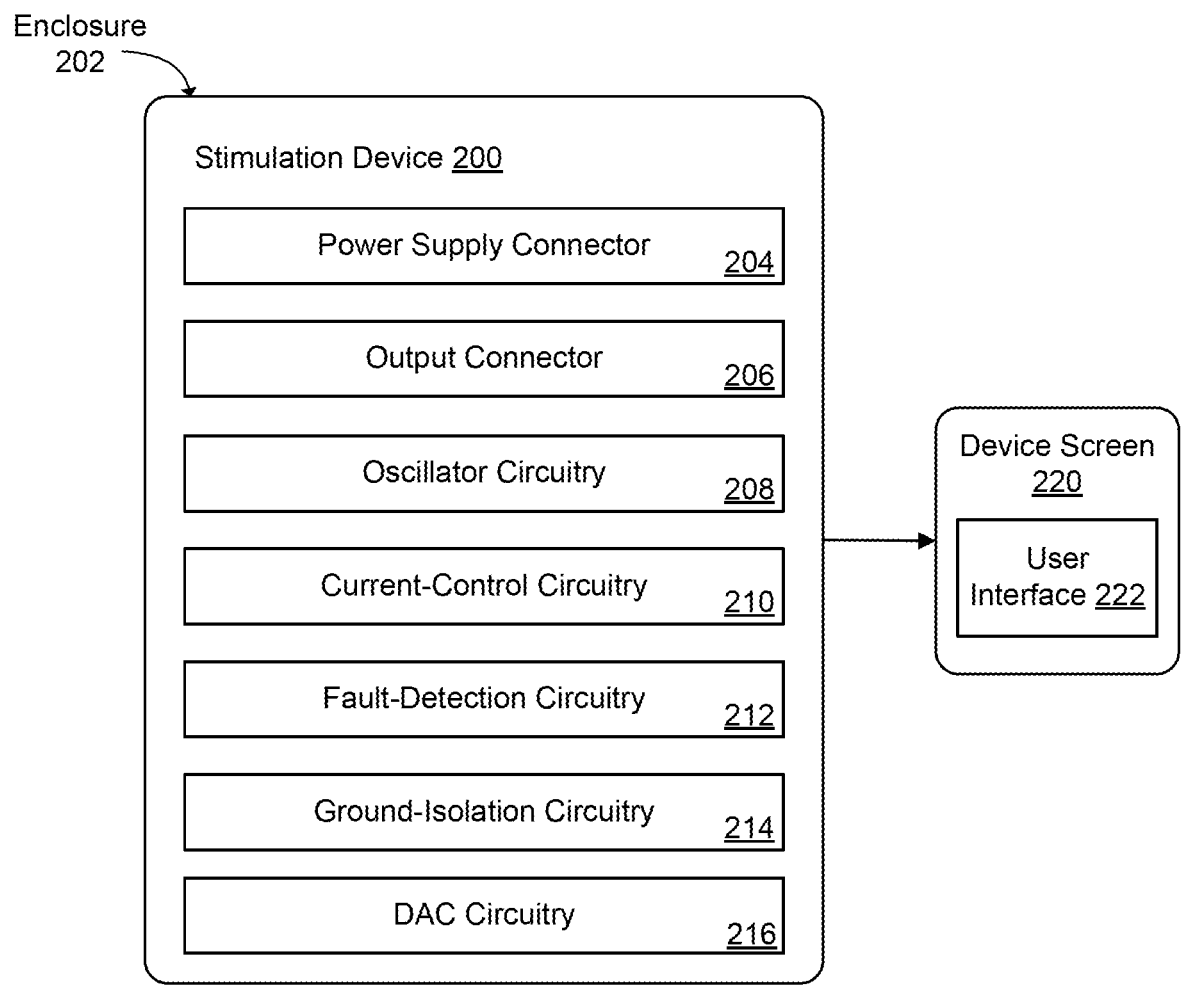
FIG. 2 illustrates a stimulation device operable to generate a high-frequency alternating current in accordance with an example.

FIG. 2 illustrates an exemplary stimulation device 200 operable to generate a high-frequency alternating current. The stimulation device 200 can be communicatively coupled to a power supply and an array of intrafascicular peripheral nerve electrodes (not shown). The stimulation device 200 can include an enclosure 202, a power supply connector 204 and an output connector 206. The enclosure 202 can provide a housing or casing for components in the stimulation device 200 (except perhaps a connection to wall power, which would be external). The power supply connector 204 can connect the stimulation device 200 to the power supply. The output connector 206 can connect the stimulation device 200 to the array of intrafascicular peripheral nerve electrodes.

In one example, the stimulation device 200 can be communicatively coupled to a device screen 220 that provides a user interface 222. The user interface 222 can provide various settings and controls to turn on and off the stimulation device 200, adjust a frequency and amplitude of the high-frequency alternating current, etc. Alternatively, the user interface 222 can be incorporated into the stimulation device 200, and the user interface 222 can include various buttons, knobs, light emitting diode (LED) indicator lights, etc. to turn on and off the stimulation device 200, adjust the frequency and amplitude of the high-frequency alternating current, etc.

In one example, the stimulation device 200 can further include oscillator circuitry 208, current-control circuitry 210, fault-detection circuitry 212 and ground-isolation circuitry 214. The oscillator circuitry 208 can produce the high-frequency alternating current, in part, using direct current or alternating current received from the power supply. The stimulation device 200 can, via the oscillator circuitry 208, generate the high-frequency alternating current as a sinusoidal current waveform that ranges in frequency from 1 to 100 kilohertz (kHz) and in amperage from 0 to 150 micro amps (mA). In addition, the oscillator circuitry 208 can include pre-programmed frequency-modulation patterns (e.g., ramp up from 2 kHz to 6 kHz over a defined time period). The oscillator circuit may consist of a Bubba oscillator, but any circuit capable of developing a sinusoidal signal with low distortion (e.g. less than 5%, and often less than 3%) may also be used. In other words, the oscillator circuitry 208 can implement these pre-programmed frequency-modulation patterns when generating the high-frequency alternating current. The current-control circuitry 210 can set a stimulation current amplitude in the 0 to 50 mA range while taking the impedance of the electrodes and neural tissue into account in accordance with user settings. The current-control circuitry can include one or more amplifiers, an oscillator circuit and a rectification and smoothing component such as a smoothing filter. Non-limiting examples of smoothing filters can include adjustable band-pass filters with a Q factor greater than ½. In one example, the current-control circuitry can additionally function as impedance-testing circuitry. A voltage can be measured across a known resistor to calculate a current while the current-control circuitry can include an unknown skin resistance, and current can be used to control the voltage as a feedback signal. The fault-detection circuitry 212 can monitor an output for signals of a short circuit, impedance spike, etc. and disconnect the power supply when faults are detected. The ground-isolation circuitry 214 (which is employed when wall power is used) can isolate the stimulation device 200 from the array of intrafascicular peripheral nerve electrodes and a subject from a wall ground connection (for safety purposes). A DAC circuitry 216 can receive digital signals and convert to analog signals for delivery to a patient. Corresponding electrodes (150 in FIG. 1) can receive the analog signals which are then transmitted into adjacent tissue of the subject 160. Notably, not all components are necessarily physically oriented within the enclosure 202. For example, the oscillator circuitry, current-control circuitry and DAC circuitry may be oriented in a non-implanted portion of the device within one or more external separate enclosures. Although wired connection can be used, optional wireless transmitters and receivers can be used to allow wireless communication of signals across the skin.

Figure 3:
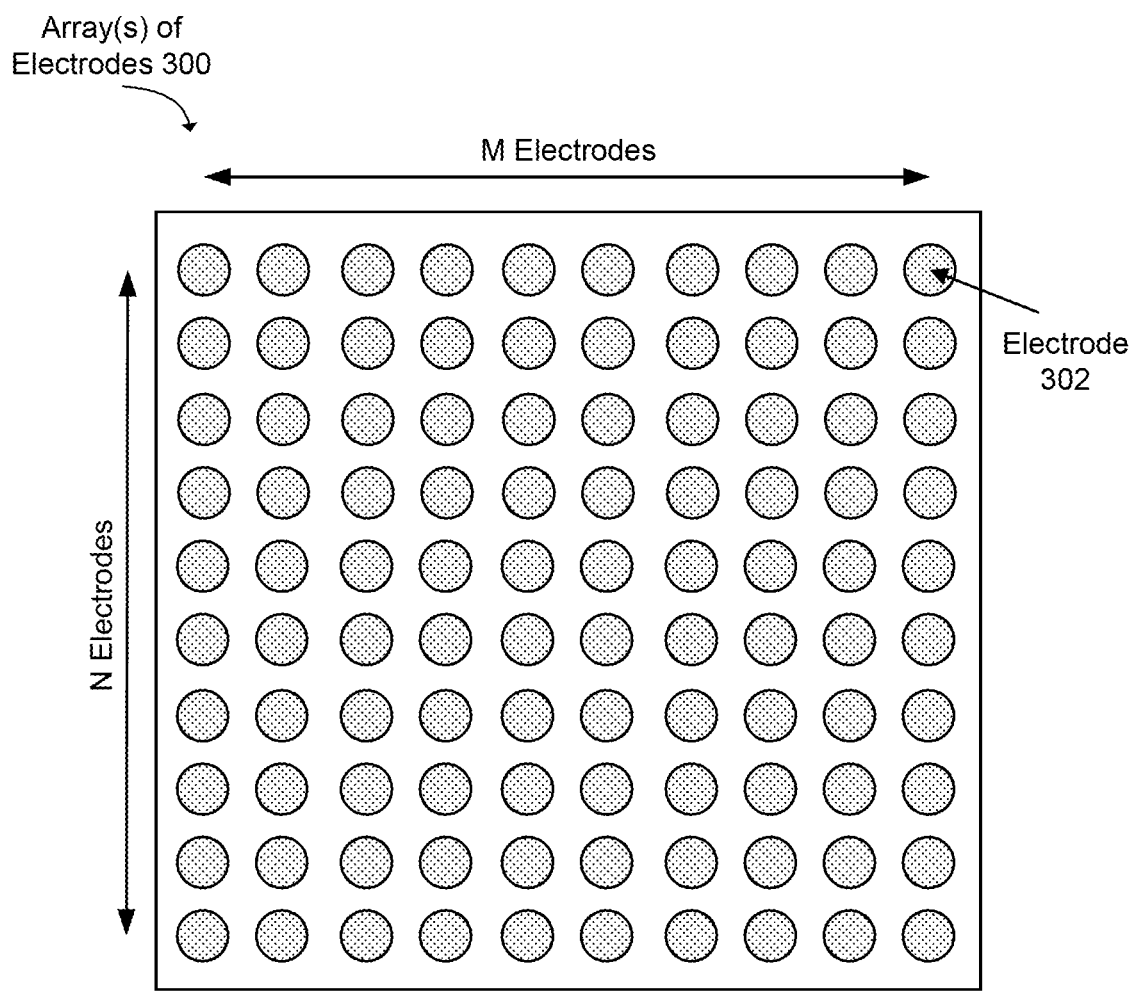
FIG. 3 illustrates an array of intrafascicular peripheral nerve electrodes in accordance with an example.

FIG. 3 illustrates an exemplary array of intrafascicular peripheral nerve electrodes 300. The array of intrafascicular peripheral nerve electrodes 300 can be an M×N matrix of individual intrafascicular peripheral nerve electrodes 302, wherein M and N are integers. The number of electrodes can generally be high such that typically from 49 to 1000, and often from 81 to 400. Regardless, at least a portion and often each of the electrodes are individually electrically addressable such that each electrode can be separately addressed to optimize stimulation to accommodate unique locations near varying tissue and individual electrode performance.

The array of intrafascicular peripheral nerve electrodes 300 can be chronically and surgically implanted in a subject. The individual intrafascicular peripheral nerve electrodes 302 can include intrafascicular nerve electrode tips. The intrafascicular nerve electrode tips can be individually coupled to selected subpopulations of peripheral nerve fibers within a peripheral nerve of the subject. More specifically, the intrafascicular nerve electrode tips can be individually coupled to selected subpopulations of peripheral nerve fibers that relate to pain. On the other hand, the intrafascicular nerve electrode tips may not be individually coupled to selected subpopulations of peripheral nerve fibers that relate to sensation and/or motor control. The intrafascicular nerve electrode tips can apply a high-frequency alternating current to the selected subpopulations of peripheral nerve fibers within the peripheral nerve of the subject, thereby blocking pain for the subject. Therefore, the individual intrafascicular peripheral nerve electrodes 302 in the array of intrafascicular peripheral nerve electrodes 300 can be distributed throughout the peripheral nerve, and the intrafascicular nerve electrode tips can be oriented in locations within the peripheral nerve that have low impedance (i.e., strong signals). Furthermore, various fiber types respond differently to stimulation. Fiber types such as IA afferents that carry proprioception information can benefit maximally, because they typically have the lowest activation threshold due to their large fiber diameters. However, as a general guideline, axons with smaller fibers, such as C fibers which transmit pain, will be less affected than larger ones due to the larger voltages necessary to activate them. However, stimulation parameters, namely frequency, and the electrodes used can specifically target more difficult to activate smaller diameter fibers.

Figure 4:
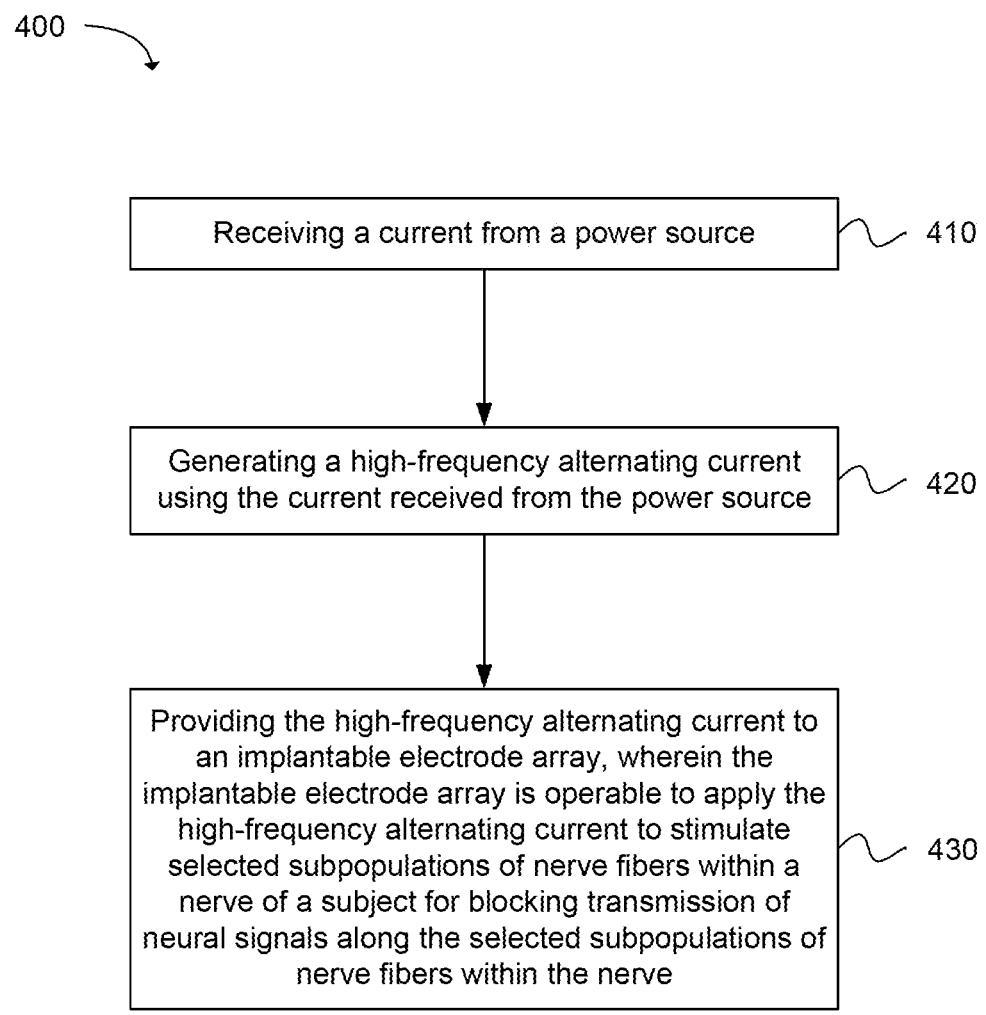
FIG. 4 depicts a flow chart of a method for electronically stimulating selected subpopulations of peripheral nerve fibers within a peripheral nerve in accordance with an example.

FIG. 4 depicts a flow chart of an exemplary method for electronically stimulating selected subpopulations of nerve fibers within a nerve. The method can include the operation of receiving a current from a power source, as in block 410. The method can include the operation of generating a high-frequency alternating current using the current received from the power source, as in block 420. The method can also include the operation of providing the high-frequency alternating current to an implantable electrode array, as in block 430. The implantable electrode array can be operable to apply the high-frequency alternating current to stimulate selected subpopulations of nerve fibers within a nerve of a subject for blocking transmission of neural signals along the selected subpopulations of nerve fibers within the nerve.

Figure 5:
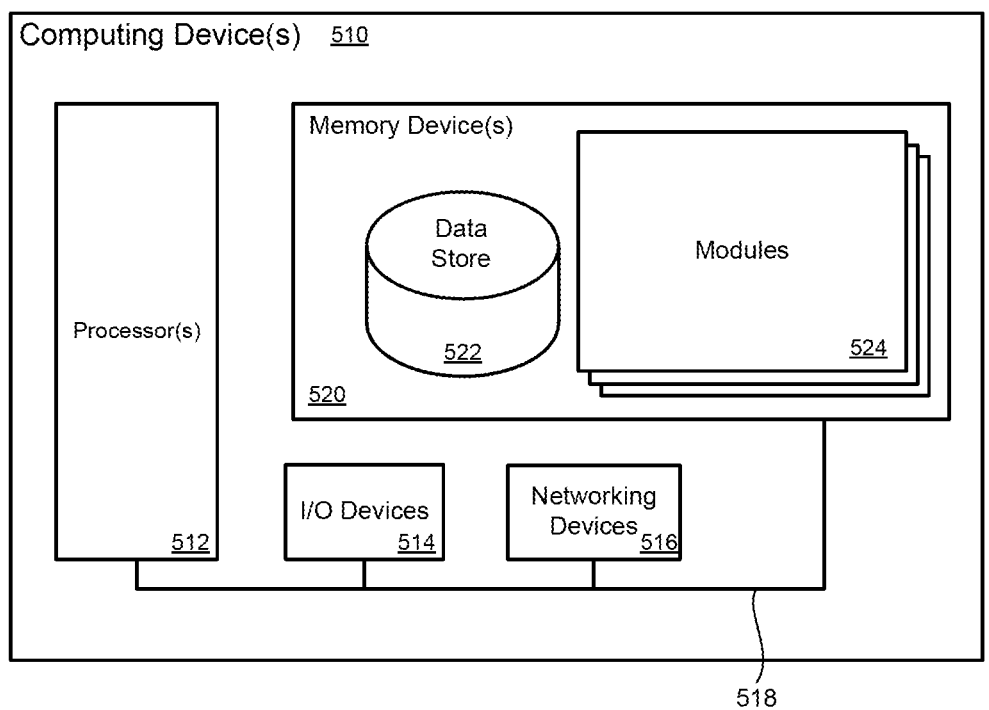
FIG. 5 is a block diagram that provides an example illustration of a computing device that may be employed in the present technology.

FIG. 5 illustrates a computing device 510 on which modules of this technology may execute. A computing device 510 is illustrated on which a high level example of the technology may be executed. The computing device 510 may include one or more processors 512 that are in communication with memory devices 520. The computing device 510 may include a local communication interface 518 for the components in the computing device. For example, the local communication interface 518 may be a local data bus and/or any related address or control busses as may be desired.

The memory device 520 may contain modules 524 that are executable by the processor(s) 512 and data for the modules 524. The modules 524 may execute functions that perform the methods described earlier. A data store 522 may also be located in the memory device 520 for storing data related to the modules 524 and other applications along with an operating system that is executable by the processor(s) 512.

Other applications may also be stored in the memory device 520 and may be executable by the processor(s) 512. Components or modules discussed in this description that may be implemented in the form of software using high programming level languages that are compiled, interpreted or executed using a hybrid of the methods.

The computing device may also have access to I/O (input/output) devices 514 that are usable by the computing devices. Networking devices 516 and similar communication devices may be included in the computing device. The networking devices 516 may be wired or wireless networking devices that connect to the internet, a LAN, WAN, or other computing network.

The components or modules that are shown as being stored in the memory device 520 may be executed by the processor(s) 512. The term "executable" may mean a program file that is in a form that may be executed by a processor 512. For example, a program in a higher level language may be compiled into machine code in a format that may be loaded into a random access portion of the memory device 520 and executed by the processor 512, or source code may be loaded by another executable program and interpreted to generate instructions in a random access portion of the memory to be executed by a processor. The executable program may be stored in any portion or component of the memory device 520. For example, the memory device 520 may be random access memory (RAM), read only memory (ROM), flash memory, a solid state drive, memory card, a hard drive, optical disk, floppy disk, magnetic tape, or any other memory components.

The processor 512 may represent multiple processors and the memory device 520 may represent multiple memory units that operate in parallel to the processing circuits. This may provide parallel processing channels for the processes and data in the system. The local interface 518 may be used as a network to facilitate communication between any of the multiple processors and multiple memories. The local interface 518 may use additional systems designed for coordinating communication such as load balancing, bulk data transfer and similar systems.

While the flowcharts presented for this technology may imply a specific order of execution, the order of execution may differ from what is illustrated. For example, the order of two more blocks may be rearranged relative to the order shown. Further, two or more blocks shown in succession may be executed in parallel or with partial parallelization. In some configurations, one or more blocks shown in the flow chart may be omitted or skipped. Any number of counters, state variables, warning semaphores, or messages might be added to the logical flow for purposes of enhanced utility, accounting, performance, measurement, troubleshooting or for similar reasons.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions and may even be distributed over several different code segments, among different programs and across several memory devices. Similarly, operational data may be identified and illustrated herein within modules and may be embodied in any suitable form and organized within any suitable type of data structure. The operational data may be collected as a single data set, or may be distributed over different locations including over different storage devices. The modules may be passive or active, including agents operable to perform desired functions.

The technology described here may also be stored on a computer readable storage medium that includes volatile and non-volatile, removable and non-removable media implemented with any technology for the storage of information such as computer readable instructions, data structures, program modules, or other data. Computer readable storage media include, but are not limited to, non-transitory media such as RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which may be used to store the desired information and described technology.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example and not limitation, communication media includes wired media such as a wired network or direct-wired connection and wireless media such as acoustic, radio frequency, infrared and other wireless media. The term computer readable media as used herein includes communication media.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described technology.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. An electronic peripheral nerve stimulation system, comprising:
   a stimulation device operable to generate a high-frequency alternating current; and
   an electrode array operable to apply the high-frequency alternating current received from the stimulation device to selected subpopulations of peripheral nerve fibers within a peripheral nerve to block transmission of neural signals along the selected subpopulations of peripheral nerve fibers within the peripheral nerve,
   wherein the electrode array is an array of intrafascicular peripheral nerve electrodes, and wherein intrafascicular peripheral nerve electrode tips are individually coupled to the selected subpopulations of peripheral nerve fibers within the peripheral nerve,
   wherein the high-frequency alternating current applied to the array of intrafascicular peripheral nerve electrodes is between 0 and 150 micro amps ($\mu A$).

2. The electronic peripheral nerve stimulation system of claim 1, wherein the electrode array is operable to:
   apply the high-frequency alternating current to selected subpopulations of peripheral nerve fibers within the peripheral nerve to block pain for a subject; and
   not apply the high-frequency alternating current to selected subpopulations of peripheral nerve fibers within the peripheral nerve to preserve sensation and motor function for the subject.

3. The electronic peripheral nerve stimulation system of claim 1, wherein the array of intrafascicular peripheral nerve electrodes is a penetrating microneedle array.

4. The system of claim 3, wherein the penetrating microneedle array is one or more of a Utah Electrode Array (UEA), a Utah Slant Electrode Array (USEA), a Longitudinal Intrafascicular Electrode array (LIFE), a Transverse Intrafascicular Multichannel Electrode array (TIME), and a Michigan array.

5. The electronic peripheral nerve stimulation system of claim 1, wherein the stimulation device is further operable to generate the high-frequency alternating current to be a waveform ranging from 1 to 100 kilohertz (kHz).

6. The electronic peripheral nerve stimulation system of claim 1, wherein the electrode array is chronically and surgically implantable in a subject.

7. The electronic peripheral nerve stimulation system of claim 1, wherein the stimulation device is operable to ramp up the high-frequency alternating current starting from 0 micro amps to a defined current level in accordance with a defined increase function.

8. The electronic peripheral nerve stimulation system of claim 1, wherein the stimulation device is operable to provide the high-frequency alternating current to the electrode array via transcutanenous wires or via a wireless technology.

9. The electronic peripheral nerve stimulation system of claim 1, further comprising a power supply that provides direct current or alternating current to the stimulation device for generation of the high-frequency alternating current, wherein the direct current or the alternating current is provided via batteries or via a wall-plug adapter or via both batteries and wall-plug adapter.

10. The electronic peripheral nerve stimulation system of claim 1, further comprising a user interface that enables adjustment of at least one of a frequency and amplitude of the high-frequency alternating current.

11. The electronic peripheral nerve stimulation system of claim 1, wherein the stimulation device is portable or non-portable.

12. The electronic peripheral nerve stimulation system of claim 1, wherein the transmission of neural signals along the selected subpopulations of peripheral nerve fibers within the peripheral nerve is unblocked when the high-frequency alternating current stops being applied to the selected subpopulations of peripheral nerve fibers within the peripheral nerve.

13. The electronic peripheral nerve stimulation system of claim 1, wherein the stimulation device is further operable to apply a shift correction to center the high-frequency alternating current at 0 volts over a period of time.

14. The system of claim 1, wherein the array of intrafascicular peripheral nerve electrodes is an M×N array of electrodes having from 25 to 1000 electrodes.

15. A system for performing peripheral nerve stimulation, the system comprising:
a power source;
a stimulation device operable to generate a high-frequency alternating current using current received from the power source; and
an implantable electrode array communicatively coupled to the stimulation device,
wherein the implantable electrode array is operable to apply the high-frequency alternating current received from the stimulation device to selected subpopulations of peripheral nerve fibers within a peripheral nerve of a subject to block transmission of neural signals along the selected subpopulations of peripheral nerve fibers within the peripheral nerve,
wherein the implantable electrode array is an array of intrafascicular peripheral nerve electrodes, and wherein intrafascicular peripheral nerve electrode tips are individually coupled to the selected subpopulations of peripheral nerve fibers within the peripheral nerve,
wherein the high-frequency alternating current applied to the array of intrafascicular peripheral nerve electrodes is between 0 and 150 micro amps (µA).

16. The system of claim 15, wherein the electrode array is operable to:
apply the high-frequency alternating current to selected subpopulations of peripheral nerve fibers within the peripheral nerve to block pain for a subject; and
not apply the high-frequency alternating current to selected subpopulations of peripheral nerve fibers within the peripheral nerve to preserve sensation and motor function for the subject.

17. The system of claim 15, wherein the array of intrafascicular peripheral nerve electrodes is a penetrating microneedle array.

18. The system of claim 15, wherein the stimulation device is operable to ramp up the high-frequency alternating current starting from 0 micro amps to a defined current level in accordance with a defined increase function.

19. The system of claim 15, wherein the stimulation device is operable to provide the high-frequency alternating current to the electrode array via transcutanenous wires or via a wireless technology.

20. The system of claim 15, wherein the transmission of neural signals along the selected subpopulations of peripheral nerve fibers within the peripheral nerve is unblocked when the high-frequency alternating current stops being applied to the selected subpopulations of peripheral nerve fibers within the peripheral nerve.

21. The system of claim 15, wherein the stimulation device is further operable to apply a shift correction to center the high-frequency alternating current at 0 volts over a period of time.

22. A method for electronically stimulating selected subpopulations of peripheral nerve fibers within a peripheral nerve, the method comprising:
receiving a current from a power source;
generating a high-frequency alternating current using the current received from the power source; and
providing the high-frequency alternating current to an implantable electrode array,
wherein the implantable electrode array is operable to apply the high-frequency alternating current to stimulate selected subpopulations of peripheral nerve fibers within a nerve of a peripheral subject for blocking transmission of neural signals along the selected subpopulations of peripheral nerve fibers within the peripheral nerve,
wherein the implantable electrode array is an array of intrafascicular peripheral nerve electrodes which is a penetrating microneedle array, and wherein intrafascicular peripheral nerve electrode tips are individually coupled to the selected subpopulations of peripheral nerve fibers within the peripheral nerve,
wherein the high-frequency alternating current applied to the array of intrafascicular peripheral nerve electrodes is between 0 and 150 micro amps (µA).

23. The method of claim 22, further comprising ramping up the high-frequency alternating current starting from 0 micro amps to a defined current level in accordance with a defined increase function.

24. The method of claim 22, further comprising applying a shift correction to center the high-frequency alternating current at 0 volts over a period of time.

25. The method of claim 22, wherein the high-frequency alternating current is a waveform ranging from 1 to 100 kilohertz (kHz).

* * * * *